United States Patent [19]

Woodward

[11] Patent Number: 4,840,904
[45] Date of Patent: Jun. 20, 1989

[54] RECOVERY AND REUSE OF CELLULASE CATALYST IN AN EXZYMATIC CELLULOSE HYDROLYSIS PROCESS

[75] Inventor: Jonathan Woodward, Oak Ridge, Tenn.

[73] Assignee: The United States of America as represented by the United States Department of Energy, Washington, D.C.

[21] Appl. No.: 98,242

[22] Filed: Sep. 18, 1987

[51] Int. Cl.$^4$ .......................... C12P 7/10; C12P 19/02
[52] U.S. Cl. ..................................... 435/165; 435/99; 435/105; 435/161
[58] Field of Search .......................... 435/99, 161–165, 435/252, 209, 815, 813

[56] References Cited

U.S. PATENT DOCUMENTS

| | | | |
|---|---|---|---|
| 3,943,072 | 3/1976 | Thomson et al. | 502/412 |
| 4,220,721 | 9/1980 | Emert et al. | 435/161 |
| 4,336,161 | 6/1982 | Rosevear et al. | 502/7 |
| 4,443,339 | 4/1984 | Rosevear et al. | 210/635 |

OTHER PUBLICATIONS

Mandells, "Applications of cellulases," Biochemical Society Transactions.
Tierneld et al. "Enzyme Recycling in Cellulose Hydrolysis by Combined Use of Aqueous Two-Phase Systems and Ultrafiltration," Biotechnology and Bioengineering Symp. No. 15 (1985).
Maxrosorb Kax Composites, Information Bulletin, Feb. 87.
Chernoglazov et al, "Production of Highly Purified Multiple Engo-1, 4-B-Glucanases From . . . ," 1986 Plenum Publishing Corporation.
Woodward et al, "Affinity Chromatography of B--Glucosidase and Endo-B-Glucanase from Aspergillus . . . ," Chemical Technology Division, Oak Ridge National Labratory.
Woodward et al, "The Adsorption of Trichoderma reesei C30 Cellulase Protein to Protein Adsorbents: Application to Cellulase Recovery and Reuse".
Rogalski et al, "Immobilization of cellulase and D-xylanase complexes from Asperigillus terreus F-413 on controlled porosity glasses," Enzyme Microb. Technol., 1985, vol. 7, Aug.
Klyoxov et al, "Enzymatic Conversion of Cellulosic Materials to Sugars and Alcohol," Applied Biochemistry and Biotechnology, vol. 12, 1986.
Woodward et al, "Development of a Method for the Recovery of the Enzyme Cellulase from Aqueous Solution," in Proceeding of the World Congress of Chemical Engineering (1986).
Karube et al, "Hydrolysis of Cellulose in a Cellulase-Bed Reactor," Biotechnology and Bioengineering, vol. XIX, pp. 1183–1191 (1977).
Woodward et al, "Immobilization of cellulase through its carbohydrate side chains-a rationale for its recovery and reuse," Enzyme Microb. Technol., 1982, vol. 4, Jul.
Fadda et al. "Highly efficient solubilization of natural lignocellulosic meterials by a commercial cellulase immobilized on various solid supports," Applied Microbiology and Biotechnology, Springer-Verlas 1984.

Primary Examiner—Barry S. Richman
Assistant Examiner—T. J. Wallen
Attorney, Agent, or Firm—Katherine P. Lovingood; Stephen D. Hamel; William R. Moser

[57] ABSTRACT

A process for recovering cellulase from the hydrolysis of cellulose, and reusing it in subsequent hydrolyois procedures. The process utilizes a commercial adsorbent that efficiently removes cellulase from reaction products which can be easily removed by simple decantation.

4 Claims, 1 Drawing Sheet

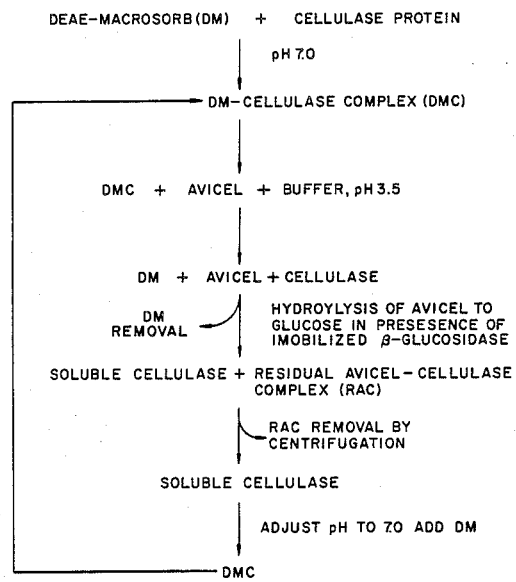

```
DEAE-MACROSORB(DM)   +   CELLULASE PROTEIN
                    │
                    │ pH 7.0
                    ▼
     ┌──────► DM-CELLULASE COMPLEX (DMC)
     │              │
     │              ▼
     │    DMC  +  AVICEL  +  BUFFER, pH 3.5
     │              │
     │              ▼
     │       DM  +  AVICEL + CELLULASE
     │         DM  ╱│  HYDROYLSIS OF AVICEL TO
     │      REMOVAL │  GLUCOSE IN PRESESENCE OF
     │              │  IMOBILIZED β-GLUCOSIDASE
     │              ▼
     │   SOLUBLE CELLULASE + RESIDUAL AVICEL-CELLULASE
     │                          COMPLEX (RAC)
     │              │
     │              │╲ RAC REMOVAL BY
     │              │ ╱CENTRIFUGATION
     │              ▼
     │       SOLUBLE CELLULASE
     │              │
     │              │ ADJUST pH TO 7.0 ADD DM
     │              ▼
     └────── DMC
```

RECOVERY AND REUSE OF CELLULASE CATALYST IN AN EXZYMATIC CELLULOSE HYDROLYSIS PROCESS

This invention relates to a process for recovering cellulase from the process of hydrolysis of cellulose and was developed pursuant to a contract with the U.S. Department of Energy.

BACKGROUND

Cellulose is the principal component of biomass, a renewable source of energy derived from woody plants, agricultural residues, and other similar forms of biological matter. It is a polymer that can be hydrolyzed to yield glucose, and subsequently transformed by fermentation to yield fuels and chemicals. The enzyme cellulase, a biological catalyst composed of several proteins, is required to achieve rapid cellulose hydrolysis; however, use of this catalyst is not practical at present because it is very expensive and no satisfactory method has been developed to recover it from the hydrolysate mixture.

The enzymatic hydrolysis of cellulose could become a more economical process if the enzyme could be recovered from the reaction mixture in active form and reused several times. This could be achieved if an immobilized cellulase were used to hydrolyze lignocellulosic substrates. However, the use of an immobilized enzyme to catalyze the hydrolysis of an insoluble substrate is difficult because effective interaction between enzyme and substrate would be greatly impaired by the enzyme's immobility.

There are, however, some reports describing the use of immobilized cellulase to hydrolyze insoluble cellulose. For example, cellulase has been immobilized in a collagen fibril matrix. Although details on the recovery of activity after immobilization were not reported, the immobilized enzyme in a fluidized bed reactor reportedly hydrolyzed insoluble microcrystalline cellulose, tradename Avicel, manufactured by F.M.C. Corporation of Philadelphia, Pa., (0.55% w/v) circulating through the bed. Greater than 80% hydrolysis of the substrate was achieved after 160 H at 30° C. Furthermore, no leakage of the enzyme was reported to occur, which suggests that intimate association between the immobilized enzyme and insoluble cellulose had to occur, even during constant circulation of substrate.

The cellulase complex of *Trichoderma reesei* C30 has been immobilized by covalent coupling to cyanogen bromide-activated Sepharose after aminolylation of the carbohydrate side chains of the enzyme with ethylenediamine. However, more than 90% of the Avicelase activity was lost when the cellulase was immobilized by this method. Cellulase from *Aspergillus terreus* has been attached to controlled pose glass and claimed 72% retention of activity. However, enzyme leakage from the support was the cause of the high activity in this case. Generally, covalently immobilized cellulases are not useful because of their low reactivity towards cellulose.

In the Soviet Union cellulose has been enzymatically converted to glucose in columnar reactor, and released cellulase protein is readsorbed on excess or newly added cellulose. Although the use of cellulose as an adsorbent improved the economy of enzyme utilization, the β-glucosidase component of cellulase is poorly adsorbed on cellulose and the affinity of different endoglucanases from the same and different species differs widely. Therefore key cellulase enzyme components which poorly adsorb on cellulose, but nevertheless are essential for complete hydrolysis of cellulose to glucose, could be lost if cellulose were used as the adsorbent.

Other examples of adsorbents that have been used in an attempt to bind cellulase include Dowex Anion Exchange Resin, Ceramic-$SiO_2$ $ZrO_2$/MgO PSZ (partialy stabilized zirconia), FSZ (fused stabilized zirconia), Macrosorb titania and Macrosorb calcium phosphate; however, no attempts resulted in success. There is no clear way to predetermine which adsorbent may be useful in separating cellulase from a reaction solution. Therefore there is a need to develop a process to recover the cellulase and reuse it in subsequent hydrolyses processes.

SUMMARY OF THE INVENTION

In view of the above-mentioned need it is an object of this invention to provide a process for removal and recovery of the enzyme cellulase from a cellulose hydroysis product and condition it for reuse.

It is also the object of this invention to recycle the cellulase catalyst in a cellulose hydrolysis process. These and other objects will become obvious to persons skilled in the art upon study of the specifications and appended claims.

The invention is a process for recovering cellulase subsequent to the hydrolysis of cellulose comprising, at a basic pH contacting a solution of reactant products with DEAE-Macrosorb absorbent available from Sterling Organics, Renssalaer, N.Y., thereby resulting in the adsorption of cellulase on the adsorbent, and then contacting the cellulase and adsorbent with a solution having an acidic pH to separate the cellulose from the absorbent.

This adsorbent, developed from chromatographic separations, efficiently attaches to cellulase in the presence of reaction products and its density enables easy separation by simple decantation. This is a significant advance in the art since the failure to be able to recover cellulase has been a continuing problem in attempts to make cellulose an economical source of alcohol fuel.

BRIEF DESCRIPTION OF THE DRAWING

The FIGURE is a schematic diagram representing a proposed process sequence of the claimed invention.

DETAILED DESCRIPTION OF THE PREFERRED EMBODIMENT

Recently, several macroporous Kiesselguhr granules which are trade named Macrosorb have become commercially available from Sterling Organics, Renssalaer, N.Y. There are several kinds of Macrosorb, one of which is called DEAE-Macrosorb, that can be used in the purification of proteins. Proteins will absorb to this material under appropriate conditions and can then be desorbed from it when the conditions are changed.

The method for cellulase recovery described herein is based upon the adsorption to DEAE-Macrosorb of cellulase protein present in cellulose hydrolysates and the subsequent removal of the adsorbed cellulase enzyme from the hydrolysate.

Undigested solids are removed from the product at the completion of hydrolysis and the pH of the particle-free solution is adjusted to 5.0-8.0. A sufficient amount of DEAE-Macrosorb is added to adsorb the cellulase enzyme from the solution. The adsorbent/cellulase complex is separated from the hydrolysis product and then placed in a solution having a pH between 2.5 and 4.0 to separate the cellulase from the adsorbent and redissolve said cellulase. The cellulase solution is ready for fresh substrate to be added to start the reaction again.

EXAMPLE 1

In a practical process, cellulose was mixed with cellulase protein in aqueous medium under appropriate conditions, and hydrolysis proceeded. As in a typical enzymatic cellulose hydrolysis, not all of the cellulose was hydrolyzed so that at the completion of hydrolysis when there was no further glucose production, a portion of the cellulose remained unhydrolyzed. The recovery of the cellulase protein used in the hydrolysis was achieved by adding DEAE-Macrosorb to the mixture, which adsorbed the cellulase protein, followed by its separation by simple decantation.

EXAMPLE 2

DEAE-Macrosorb was washed thoroughly with 50 mM sodium acetate buffer, pH 5.0. The support (1 g) was shaken in a rotary shaking water bath at 30° C. for 30 min. with 5.4 mg of cellulase protein of 10 mL of the same buffer. The supernatant was assayed for protein and the amount of cellulase protein adsorbed to the Macrosorb extrapolated.

It is important that the recovery of cellulase protein occur in the presence of glucose as well as ethanol if the glucose ferments simultaneously. DEAE-Macrosorb has the same adsorption capacity for protein in the presence of 0.5M glucose, and this capacity is only slightly reduced in the presence of 10% (v/v) ethanol. See Table 1.

TABLE 1

| Adsorption of cellulase protein to DEAE-Macrosorb | |
|---|---|
| Additive | *Percentage of cellulase protein adsorbed |
| None | 46 |
| Glucose (0.5M) | 48 |
| Ethanol (10% v/v) | 39 |

*Values given are the percentages of cellulase protein (i.e., 5.4 mg) initially contacted with the support that is adsorbed to the Macrosorb preparation. Adsorption conducted in 50 mM sodium acetate buffer, pH 5.0.

EXAMPLE 3

Several experiments were performed to determine the optimum pH at which DEAE-Macrosorb would adsorb cellulase. The effect of pH on the adsorption of cellulase protein to DEAE-Macrosorb is seen in Table 2.

A greater percentage of protein is adsorbed to DEAE-Macrosorb at the higher pH values. The higher percentage of protein bound at pH 5.0 compared to that observed previously as shown in Table 1 is due to the fact that a lower ionic strength buffer was used in this example. It is possible that an even higher percentage of protein could be bound if the pH were even higher. However, due consideration should be given to the stability of the cellulase protein at the higher pH values.

TABLE 2

| The effect of pH on the adsorption of cellulase protein to DEAE-Macrosorb | | |
|---|---|---|
| ph | Bound protein (mg) | Bound protein (% of total) |
| 3.5 | 1.35 | 25 |
| 5.0 | 3.55 | 66 |
| 6.0 | 4.0 | 74 |
| 7.0 | 4.1 | 76 |

10 mM sodium acetate buffer was used for pH 3.5, 5.0, and 6.0; 10 mM Hepes buffer was used for pH 7.0; 5.4 mg cellulase protein was initially contacted with the support.

EXAMPLE 4

Based upon the data and observations given in Examples 1 to 3, a scheme shown in the FIGURE was devised whereby cellulase adsorbed on this support could be used, recovered from the reaction medium and reused. To determine the technical feasibility of the scheme, cellulase protein was adsorbed on DEAE-Macrosorb at pH 7.0 to give 4.1 mg protein bound per gram of support. The support was then shaken for 60 min. at 23° C. in 20 mL of 10 mM sodium acetate buffer, pH 3.5, after which time the amount of protein in the decanted supernatant was 3.41 mg (−83% of the initial protein bound to the support). Avicel (100 mg) and 1 g of β-glucosidase immobilized on Macrosorb was added to the supernatant and glucose formation monitored. the β-glucosidase, a component of cellulase, enhances the hydrolysis reaction and is routinely added to such reactions by persons skilled in the art. In a control, 3.41 mg of soluble cellulase protein was mixed with the substrate and immobilized β-glucosidase. The cellulose hydrolysis was carried out at pH 3.5 rather than pH 5.0 since the majority of cellulase protein does not bind to DEAE-Macrosorb at pH 3.5 and the activity of Trichoderma reesei C30 cellulase towards Avicel at pH 3.5 is only 15% lower than at pH 5.0.

The amount of glucose produced by 3.41 mg of cellulase protein that was originally adsorbed on Macrosorb and by the same amount of soluble cellulase protein is shown in Table 3.

At the end of the hydrolysis, the reaction mixtures were centrifuged, the supernatants adjusted to pH 7.0 with 1N sodium hydroxide, and their protein concentrations determined. DEAE-Macrosorb (1 g), equilibrated with pH 7.0 buffer, was added to each of the supernatants and shaken at 30° C. for 30 min. The protein concentration of the supernatants was redetermined from which the amount of protein readsorbed to DEAE-Macrosorb was extrapolated. These data are summarized in Table 4, and indicate that 75% and 68% of the hydrolysate protein were recovered when the source of cellulase protein was originally soluble or immobilized, respectively. Thus, of the initial originally immobilized cellulase protein (3.4 mg), 50% was recovered by its readsorption onto DEAE-Macrosorb.

Reuse of the recovered cellulase protein was achieved by shaking the support in buffer, pH 3.5, to desorb the protein, decanting the supernatant, followed by addition of the substrate and 1 g immobilized β-glucosidase. In control experiments, cellulose hydrolysis was carried out using the same amount of cellulase protein that was desorbed from the support plus the immobilized β-glucosidase. Glucose formation was monitored in both cases. The data in Table 5 show that soluble cellulase protein that has been used to hydrolyze cellulose over a 68-h period can be recovered from solution and reused again.

TABLE 3
Avicel hydrolysis by originally immobilized and soluble cellulase protein

| Time (h) | Total glucose (mg) | |
|---|---|---|
| | Soluble cellulase protein | Originally immobilized cellulase protein |
| 1 | 7.3 | 6.3 |
| 19 | 47.2 | 37.1 |
| 43 | 67.7 | 54.0 |
| 68 | 73.4 | 61.6 |

Avicel (100 mg) was incubated at 30° C. in a shaking water bath in 20 mL of 10mM, sodium acetate buffer, pH 3.5, containing 1 g immobilized β-glucosidase and 3.41 mg of cellulase protein.

TABLE 4
Recovery of cellulase protein from avicel hydrolysates by readsorption on DEAE-Macrosorb

| Protein source | Protein in hydrolysate (mg) | Protein readsorbed on 1 g DEAE-Macrosorb (mg) |
|---|---|---|
| Soluble cellulase protein (control) | 1.6 | 1.2 |
| Originally immobilized cellulase protein | 2.5 | 1.7 |

TABLE 5
Reuse of cellulase protein recovered from avicel hydrolysates

| Protein source | Protein desorbed into solution at pH 3.5 (mg) | Glucose produced at 68 h (mg) |
|---|---|---|
| Soluble cellulase protein (control) | 1.0 | 47.9 (55.4)* |
| Originally immobilized cellulase protein | 1.5 | 45.4 (55.4)* |

*Values in parentheses represent the determined amount of glucose produced by 1.0 and 1.5 mg of fresh soluble cellulase protein not previously used and recovered.

As another embodiment, the DEAE-Macrosorb could be placed in a column through which cellulosic hydrolysates could continuously flow and from which cellulase protein could be extracted, the process thus operating in a continuous rather than a batch mode. Without further elaboration, it is believed that one skilled in the art can, using the preceding description, utilize the present invention to its fullest extent. The specific embodiments are to be construed as merely illustrative and not limitative of the remainder of the disclosure.

The process of finding an effective adsorbent for a specific is difficult since it is composed of a number of proteins and the chemical structure of proteins varies greatly making an adsorbent that is suitable for certain proteins unsuitable for specific enzyme adsorption. Although information available on the commercial adsorbent of the claimed process indicated it could be used for chromatographic separation of some proteins, there was nothing in the literature to lead one to believe that DEAE-Macrosorb would adsorb cellulase. It adsorbs cellulase by efficiently binding various protein components of cellulase.

The main advantage of the subject invention is that the cellulase protein can be adsorbed and desorbed to DEAE-Macrosorb depending on the conditions. Thus, high catalytic activity will be achieved because the enzyme is not immobilized during hydrolysis, unlike the situation when a covalently immobilized cellulase is used. The adsorbent has the added advantage of density that allows easy decantation of supernatant liquid for product and enzyme separation. The method is also flexible. For example, in a batch reactor used for cellulose hydrolysis, soluble cellulase protein can be recovered easily because of the ease by which DEAE-Macrosorb can be separated from the cellulosic residue. It would be impossible to recover cellulose protein from a batch reactor by adding fresh cellulose because undigested cellulose would be difficult if not impossible to separate. This process is a significant improvement over know methods of recovering cellulase.

Since cellulase production and use account for 60% of the total processing costs associated with the enzymatic conversion of cellulose to glucose, considerable savings could be made by enzyme recovery and reuse. In a commercial process carried out by government and industry for converting cellulose to fuels and chemicals, this development could play an important role in reducing operating costs.

I claim:

1. A process for recovering cellulase subsequent to cellulose hydrolysis comprising:
at a basic pH contacting a solution of reactant products from the hydrolysis of cellulose, including cellulase, with Kieselguhi granules adsorbent, thereby resulting in the adsorption of said cellulase on said adsorbent; contacting said cellulase and a solution having an acidic pH to separate said cellulase from said adsorbent.

2. The process of claim 1 wherein said basic pH is from above 7 to 8 and said acidic pH is from 2.5 to 4.

3. The process of claim 2 wherein said reactant products comprise glucose.

4. The process of claim 3 wherein said reactant products comprise ethanol.

* * * * *